United States Patent [19]

Schelhas et al.

[11] Patent Number: 4,715,859
[45] Date of Patent: Dec. 29, 1987

[54] HIP CUP FOR A HIP JOINT ACETABULAR PROSTHESIS

[75] Inventors: Klaus-Dieter Schelhas, Bremen; Gerd Biehl, Cologne, both of Fed. Rep. of Germany

[73] Assignee: Orthoplant Endoprothetik GmbH, Bremen, Fed. Rep. of Germany

[21] Appl. No.: 937,877

[22] Filed: Dec. 4, 1986

[51] Int. Cl.$^4$ ............................................. A61F 2/34
[52] U.S. Cl. ..................................................... 623/22
[58] Field of Search ............................. 623/22, 23, 20

[56] References Cited

U.S. PATENT DOCUMENTS 4,051,559 10/1977 Pifferi ..................................... 623/22

FOREIGN PATENT DOCUMENTS 145339   6/1985  European Pat. Off. ............... 623/22
0190981  8/1986  European Pat. Off. ............... 623/22
1943598  3/1971  Fed. Rep. of Germany ........ 623/22
2319098 11/1973  Fed. Rep. of Germany ........ 623/22
2422617  4/1975  Fed. Rep. of Germany ........ 623/22
2645101  4/1978  Fed. Rep. of Germany ........ 623/22
2911754 10/1980  Fed. Rep. of Germany ........ 623/22

Primary Examiner—Richard J. Apley
Assistant Examiner—David J. Isabella
Attorney, Agent, or Firm—Merchant, Gould, Smith, Edell, Welter & Schmidt

[57] ABSTRACT

Presented is a hip cup for a hip joint acetabular prosthesis comprising an outer cup having a hemispherical or truncated cone external form and an inner hemispherical cup that is capable of being inserted into the outer cup. Running externally about the outer shell is a self-cutting thread for cementless anchoring of the hip cup, the outer diameter of which is approximately constant over the entire axial length of the thread.

10 Claims, 2 Drawing Figures

//  4,715,859

HIP CUP FOR A HIP JOINT ACETABULAR PROSTHESIS

TECHNICAL FIELD

The invention concerns a hip joint acetabular prosthesis cup, with an outer cup having a hemispherical or truncated cone form, with an inner cup capable of being inserted into the outer cup, and with a self-cutting thread running about externally on the outer shell for cementless anchoring of the cup in the bony tissue.

BACKGROUND OF THE INVENTION

A hip joint acetabular prosthesis cup of this type is known, for example, from the German AS (Publication for Opposition) No. 24 11 617. In the case of this known cup, besides the internal diameter or root diameter of the thread, also constantly decreasing is the outer diameter of the thread—at the outer edges of the thread profile—toward the face or crown surface of the cup; the thread profile corresponds to the thread profile of the bone screw and remains approximately constant over the entire axial length of the thread in order to enable easy emplacement of the cup into the correspondingly routed-out acetabulum, without first cutting a thread in the bony tissue. Additionally, this known cup has cutouts, running from the cup rim toward the crown, into which, after implantation of the cup, the bony tissue should grow in order to improve anchoring the cup. However, it has been demonstrated that the firmness of these cementlessly installed type cups is not always quite satisfactory, particularly after longer period of use. In particular, anchoring in the region of the crown of the cup, where the natural or prosthesis femoral head is supported, often times can not withstand the considerable forces introduced into the pelvic bones over the cup, whereby undesired loosening phenomena can occur over a shorter or longer period of time.

Known from the German OS (Laid-Open Print) No. 29 11 754 or OS No. 26 45 101, are hip joint acetabular prosthesis cups that display cutouts running from the cup rim toward the crown, into which, after implanting, the bony tissue is said to grow in order to increase adherence of the cup in the bony tissue.

As compared to this, the object of the invention is to further develop a hip joint acetabular prosthesis cup of the initially mentioned art such that the bearing surface between the cup and surrounding bony tissue is enlarged.

This object is resolved in accordance with the invention by the fact that the outer diameter of the thread is approximately constant over the entire axial length of the thread.

The advantages of the invention rest particularly in the fact that the outer edge of the thread lies essentially over a circular cylinder, while the inner diameter or root diameter continually decreases toward the crown of the cup, so that the carrying (bearing) surface of the thread profile continually increases from the circular cup rim up to the crown-side end of the thread. The bony tissue that is available about the acetabulum cavity in the pelvic bone is, in this manner, utilized quite well for forming the form-closed cup/bony tissue bond, and achieves and effective interengagement of bony substance and thread. Because of the increasing thread profile toward the crown, it is possible, if required, also to decrease the axial length of the thread, and it is also possible to achieve good anchoring in a comparatively flat pelvis, whereas the known type hip cup would project from the bony tissue with part of its thread.

Preferably, the thread has a non-symmetrical profile with a thread outer edge that is offset, in the axial direction of the thread, toward the crown of the cup. Particularly preferred here is that the thread profile be convexly curved away from the plane of the annular cup edge.

Hence, in this form of embodiment, the outer edge profile is at a greater distance from the plane of the cup edge than is the heel (beginning point) of the profile. This form of embodiment has the advantage that the cup remains firmly anchored in bony tissue because of the weight-occassioned loading and the large force components in the thread axis direction that are available thereby, and does not press the surrounding bony tissue radially outwardly and thereby become loose, like in the case of known symmetrical profiles.

According to a particularly preferred form of embodiment of the invention, the outer cup has externally lying cutouts that break through the thread, increase the elasticity of the cup and, for another thing, grow full with bony tissue, thereby preventing the cup from rotating itself out. In accordance with the invention, the cutouts are disposed at an acute angle on the external surface of the cup relative the plane of the cup edge; they therefore run, for example, over large circles that run, at some lateral distance away, past the crown of the cup.

In this fashion, anchoring of the thread is better distributed over the entire periphery of the cup than in the case of known cups that have cutouts running through the crown over large circles.

Advantages of further evolutions of the invention are characterized by the features of the subclaims.

BRIEF DESCRIPTION OF THE DRAWINGS

Explained in more detail in the following with the aid of the drawing is one example of embodiment of the invention. Shown are.

DETAILED DESCRIPTION OF THE INVENTION

Figure 1:
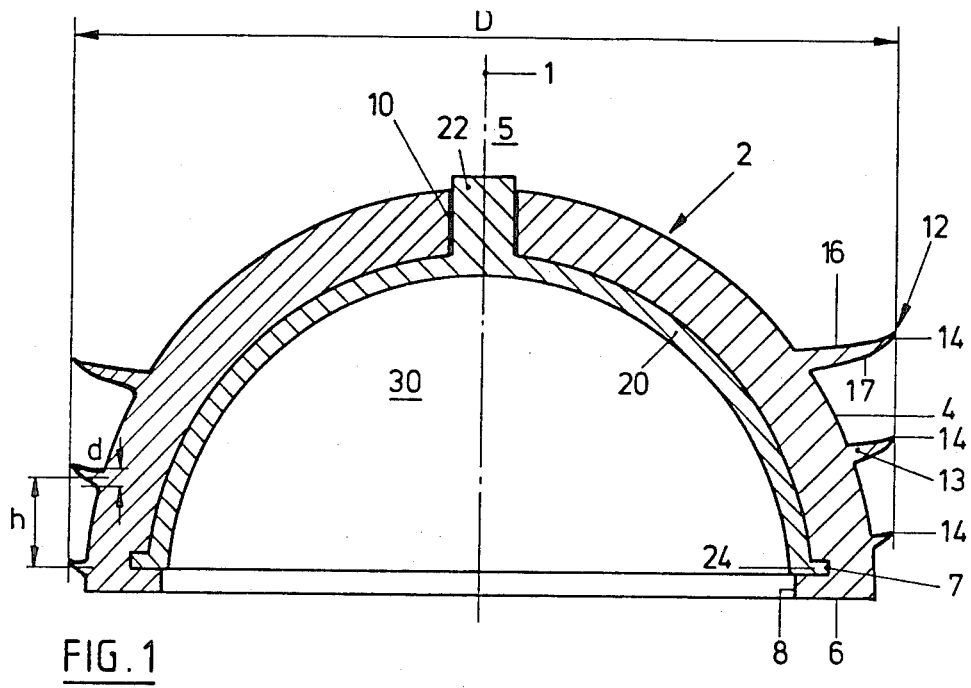
FIG. 1 - a cross section through the hip joint acetabular prosthesis cup.
Figure 2:
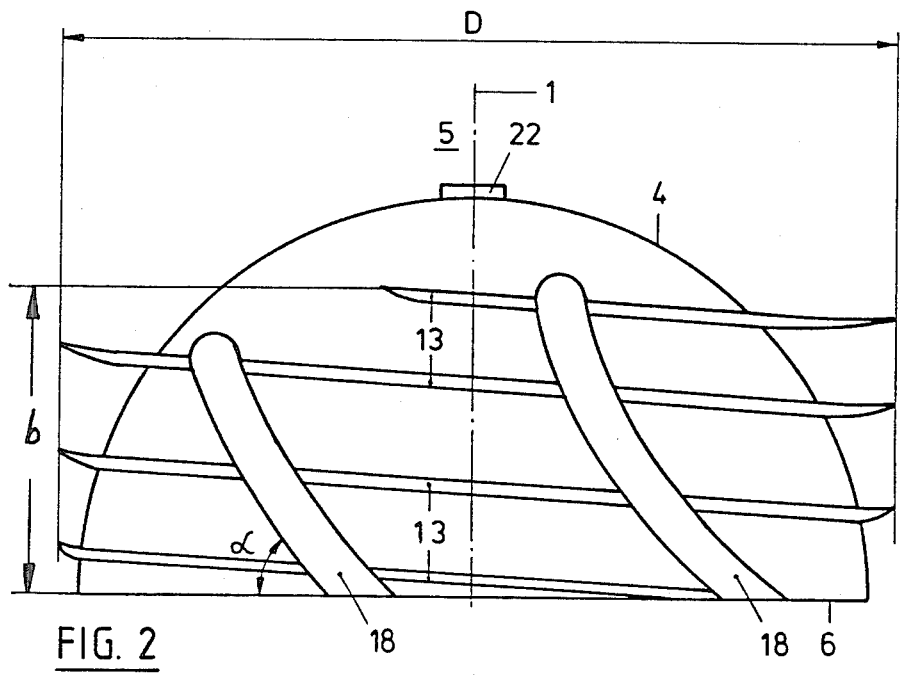
FIG. 2 - an external view of the hip joint acetabular prosthesis cup according to FIG. 1.

FIGS. 1 and 2 show a hip joint acetabular prosthesis cup 2 in a cut and in a front view. The cup 2 receives an outer cup 4 that is preferably made of metal and/or of ceramic, having a hemispherical outer form and a hemispherical inner chamber 30, into which can be placed in adapting fashion a hemispherical inner cup 20 made from plastic material or the like. For anchoring the inner cup 20, the outer cup 4 has, in the region of the annular cup edge 6, a circular groove 7 into which engages a corresponding annular shoulder of the inner cup 20. Besides this, the outer cup 4 has, at its crown 5, a central crown opening 10, preferably of a non-circular cross section, into which projects a corresponding crown stub 22 of the inner cup 20 for securing against rotation. Alternatively, the outer cup 4 can be closed off at crown 5, and it can display a central, outwardly projecting centering stub in order to be able to center the cup 2 in the desired location when implanting. The crown 5 of the outer cup can also be cut off so that there results a relatively large circular crown opening. In this form of embodiment (not represented) of the cup, the outer cup 4 has an annular configuration, and the inner cup 20 projects, with a ball section, through the crown opening of the outer cup. This form of embodiment serves in particular for implanting in flat pelvises where there is available only little bone thickness.

For cementless anchoring of the cup 2, formed externally on the outer shell 4 is a circumscribing, self-cutting thread 12 displaying a relatively large pitch that is a multiple of the profile thickness d at the beginning of the profile. While the outer form of the outer cup 4 is constructed as a hemisphere—or in the alternative forms of embodiment (not represented), can also display the form of a section of truncated cone—the outer diameter D of the thread 12 is constant over the entire axial length of the thread b so that the outer edge 14 of the thread 12 lies on a circular cylinder having a diameter D. The thread 12 has a non-symmetrical profile 13, where the thread outer edge 14—in the direction of the axis of the thread—is offset toward the crown 5, relative to the beginning of the profile.

The two thread flanks 16 and 17 that delimit the thread profile have a convex curvature relative to the plane of the annular cup edge 6. The thusly structured thread flanks 16, 17 have an increasingly greater surface toward the crown 5, and the outer edge 14 of the thread 12 is at a greater distance away from the plane of the cup edge 6 than is the beginning of thread 12 on the outer cup 4.

The outer cup has externally lying cutouts 18 that cut the thread 12 at an acute angle a, relative to the plane of the cup edge 6. The cutouts 18 can project into the cup wall by a predetermined amount; alternatively, they can be dimensioned such that they end directly at the surface of the cup wall or even in the thread profile 13 ends.

We claim:

1. Hip joint acetabular prosthesis cup comprising an outer cup having a truncated cone external form having a crown at one end and an annular cup edge at the other end, with an inner cup capable of being inserted to the outer cup, and with a self-cutting thread running about externally on the outer shell for cementless anchoring of the cup in the bony tissue, and wherein the external diameter (D) of the thread is approximately constant over the entire cup and wherein the thread has a decreasing depth as it approaches said annular cup edge.

2. Cup according to claim 1 wherein the thread displays a non-symmetrical profile with a threaded outer edge that is offset toward the crown of the cup in the axial direction of the thread.

3. Cup according to claim 2 wherein the flanks delimiting the profile of the thread are convexly curved away from the plane of the annular cup edge.

4. Cup according to claim 1 wherein the pitch (h) of the thread is a multiple of the thickness (d) of the thread profile.

5. Cup according to claim 1 wherein the outer cup displays externally lying cutouts that interrupt the thread at an acute angle (a) relative to the plane of the cup edge.

6. Hip joint acetabular prosthesis cup comprising an outer cup having a hemispherical cone external form having a crown at one end and an annular cup edge at the other end, with an inner cup capable of being inserted to the outer cup, and with a self-cutting thread running about externally on the outer shell for cementless anchoring of the cup in the bony tissue, and wherein the external diameter (D) of the thread is approximately constant over the entire cup and wherein the thread has a decreasing depth as it approaches said annular cup edge.

7. Cup according to claim 6 wherein the thread displays a non-symmetrical profile with a threaded outer edge that is offset toward the crown of the cup in the axial direction of the thread.

8. Cup according to claim 7 wherein the flanks delimiting the profile of the thread are convexly curved away from the plane of the annular cup edge.

9. Cup according to claim 6 wherein the pitch (h) of the thread is a multiple of the thickness (d) of the thread profile.

10. Cup according to claim 6 wherein the outer cup displays externally lying cutouts that interrupt the thread at an acute angle (a) relative to the plane of the cup edge.

* * * * *